United States Patent [19]

Dolinsky

[11] 4,332,559
[45] Jun. 1, 1982

[54] DENTAL FLOSS APPLICATOR AND METHOD OF ANCHORING DENTAL FLOSS UNITS AT A FRAME

[76] Inventor: Josef Dolinsky, Salzstrasse 4, D - 8960 Kempten, Fed. Rep. of Germany

[21] Appl. No.: 212,597

[22] Filed: Dec. 3, 1980

[51] Int. Cl.³ .............................................. A61C 15/00
[52] U.S. Cl. ...................................................... 132/91
[58] Field of Search ...................... 433/141; 132/91, 92

[56] References Cited

U.S. PATENT DOCUMENTS 1,166,732 1/1916 Woodhouse ........................... 132/91
3,828,804 8/1974 Ely .......................................... 132/91

FOREIGN PATENT DOCUMENTS 23268 of 1894 United Kingdom ................... 132/91

*Primary Examiner*—Robert Peshock
*Attorney, Agent, or Firm*—Alfred H. Hemingway, Jr.; Steven H. Bazerman

[57] ABSTRACT

A dental floss applicator is composed of a U-shaped frame of resilient material having a plurality of parallel slits in each one of the pair of holding arms. A plurality of unit lengths of dental floss are fastened in the slits of the arms thereby forming a dental floss curtain. The unit lengths ae provided with caps or beads at their ends and are of equal length. The interspace between a pair of caps or beads of each dental floss unit has an overdimension with respect to the space between the arms of the frame. The unit is fastened at the frame by turning the unit at least partly around the base of each arm not containing the slit of slits thereby forming a 180°-half-loop or a 360°-whole-loop of the unit. The dental floss curtain provides for a better cleaning operation between the teeth and the new fastening mode guarantees a secure arrangement of the unit at the frame even when the unit is in a slack condition.

5 Claims, 4 Drawing Figures

DENTAL FLOSS APPLICATOR AND METHOD OF ANCHORING DENTAL FLOSS UNITS AT A FRAME

BACKGROUND OF THE INVENTION

The present invention relates to a dental floss applicator for applying dental floss to teeth and to a method for fastening a dental floss unit at a holder.

Known applicators comprise a resilient U-shaped frame between the arms of which a dental floss unit of fixed length is fastened having caps or beads at its ends. The arms are provided with end-side slits respectively. The strand is inserted into the slits and the caps abut against the opposite surfaces of the arms (U.S. Pat. No. 2,180,522).

BRIEF SUMMARY OF THE INVENTION

One object of the invention is to provide a new applicator of this kind which ensures a better cleaning effect of the teeth.

A further object is to provide an applicator having a plurality of independent dental floss units arranged parallely and in a common plane thereby forming a dental floss curtain.

A further object of the invention is to provide an applicator at which dental floss units of any length measured between the end caps of which can be fastened and the tautness or slack of the units can be adjusted.

A futher object is to provide a method of anchoring a dental floss unit at the frame which guarantees a secure attachment during operation even when the unit hangs loosely between the arms of the frame.

One further object is to provide an applicator in which the opposed arms of which are provided with a plurality of substantially parallel slits respectively forming comb-like members whereby each pair of slits of both arms serve to hold one dental floss unit.

Another object is to provide an applicator at the arms of which a dental floss unit can easily be fastened having a length between its end caps or beads greater than the spacing between said arms by turning the unit at least half around each one of the arms.

Other objects and advantages will appear from detailed description which follows.

DESCRIPTION OF THE PREFERRED EMBODIMENTS

Figure 1:
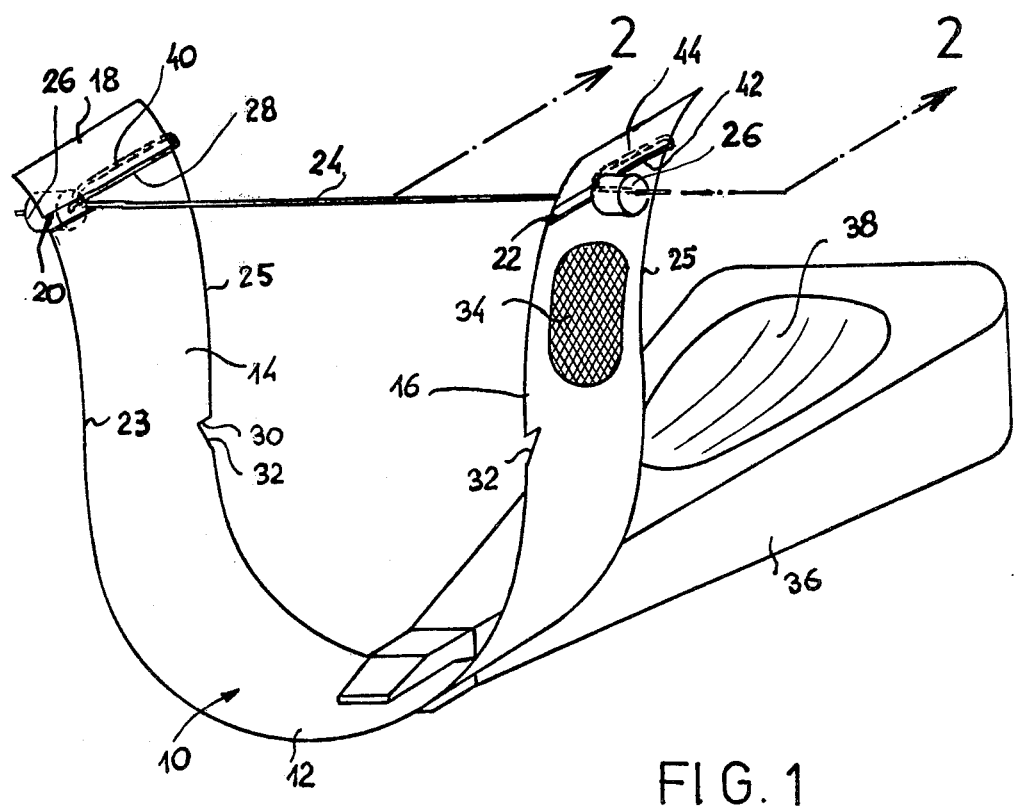
FIG. 1 is a perspective view of an embodiment of a dental floss applicator.

The applicator consists of a spring-metal flat profile frame 10 of U-shaped form having a pair of substantially parallel arms 14, 16 connected by a curved central portion 12. A slit 20, 22 respectively is provided near the end of each of the arms 14, 16. The slits extend from the front longitudinal edge 23 substantially rectangularly to the longitudinal direction of the arms and have the same length of ¼ to ¾ of the arm width. Preferably the slits 20, 22 end in the longitudinal centre plane of the frame.

A dental floss unit 24 having end caps or beads 26 is fastened at the arms 14, 16 of the frame. The lenght of the unit between the caps 26 is equal with the sum of the interspace between the outer surfaces of the arms of the frame with the arms in tensioned condition and an overdimension which amounts to a value substantially four times as long as the width of that portion of the arm which results as a difference between the whole width of the arm and the length of the slit.

The unit 24 is inserted into the slit 20 and then is pulled until the cap 26 abuts the outer surface of the arm 14. Then the unit is deflected about 90° and runs with its portion 28 along that remaining width of the arm adjoining the slit. Then the unit is deflected about 180° at the rear longitudinal edge 25 and runs with a portion 40 to the inner end of the slit 20. The unit then again is deflected about 90° and passes for a second time through the slit 20 and then is led linearly to the slit 22 of the opposite arm 16. The unit is inserted into the slit 22 and after having compressed the pair of arms 14, 16 it is led a around the arm portion adjoining slit 22 by 270° thereby forming parallel unit portions 42, 44 at the outer and inner side of the arm respectively and at last is again inserted into this slit thereby completing a 360°-loop. Then the arms are released, the unit is tensioned and the end cap abuts the outer surface of the arm 16.

Figure 2:
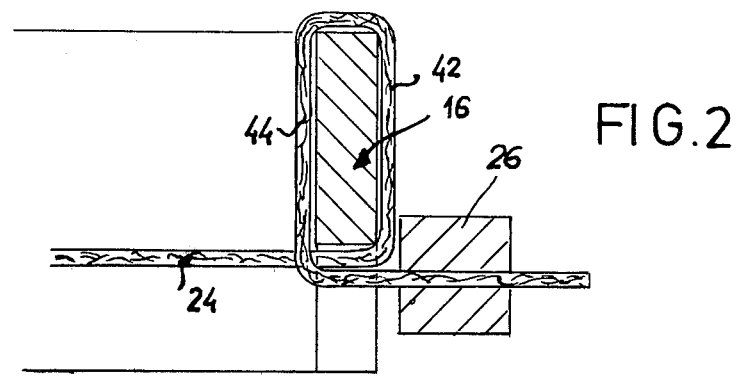
FIG. 2 is a sectional view taken along line 2—2 of FIG. 1.

FIG. 2 shows the running course of the unit 24 at the arm 16 in greater detail. Due to the fact that the unit passes through the slit twice, a self-clamping action is gained and the unit even in a slack condition can never come free from the arm. This is important because it is found that after already a short-period use of the applicator the unit is lengthened or expanded and becomes slack or loose but nevertheless the ends of the unit remain fixed. The unit can lengthen itself up to 50 percent and even in this condition it can be used. It can tightened again by pulling one of the end caps 26 and then the free end can be turned around the arm for a second time.

The applicator 10 is provided with a handle 36 comprising a finger grip 39. Instead of that in a simpler embodiment the frame can be used without a handle but with finger grips 34 at the arms of which. Notches 30 forming knife edges 32 are provided to separate a unit from a supply.

Instead of at least one of the pair of the 360°-loops a half loop can be used in which the cap or bead 26 is brought in abutment with the inner surface of one of the arms 14, 16. The unit passes through the slit of the respective arm then is deflected and runs—as the portion 40—along the outer surface to the longitudinal edge, is deflected again there and then runs linearly to the opposite arm where—in similar manner—either a 180°-loop is formed so that the other cap abuts the inner surface of this opposite arm or a 360°-loop is formed by leading the unit twice through the slit, so that the cap contacts the outer surface of the arm. By choosing any combination of one or two 180°-loops and/or one or more 360°-loops the unit can be fastened without any slack independently on its actual length. Because of the spring effect of the arms differences of the actual length of the units are compensated.

Figure 3:
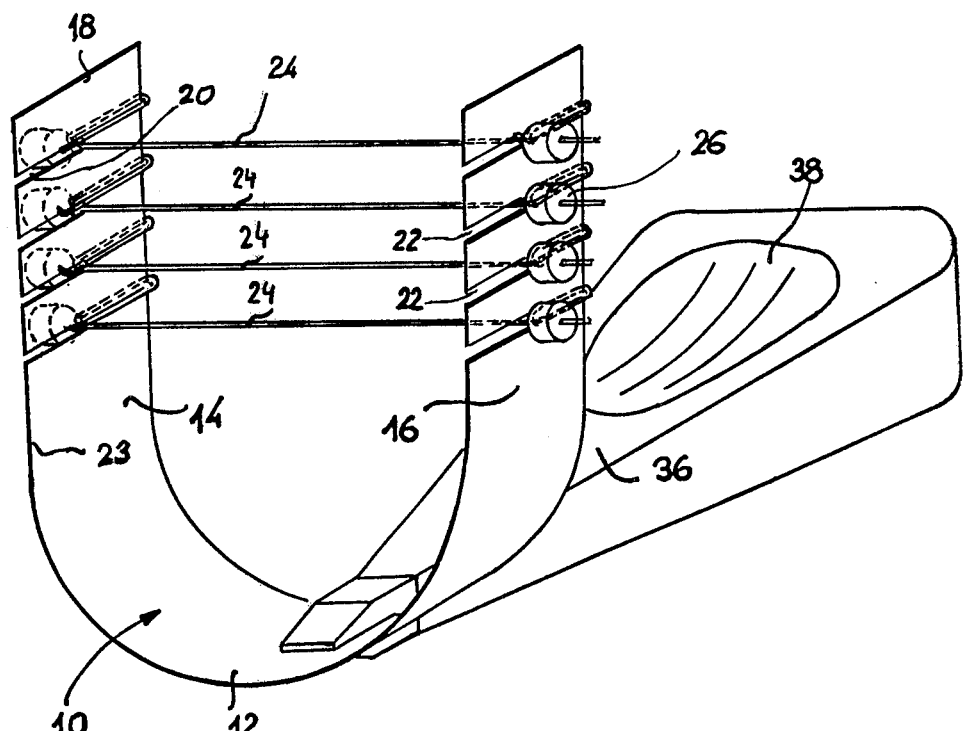
FIG. 3 is a perspective view of another embodiment of an applicator designed for attachment of a plurality of dental floss units.

FIG. 3 shows an applicator having parallel arms 14, 16. Both arms are provided with a plurality of slits respectively of equal number. The slits 20 or 22 of equal length are in parallel relationship. Corresponding pairs of slits in both arms are equally spaced, so that a plurality of parallel dental floss units can be fastened whereby a dental floss curtain is formed having a much higher cleaning surface as compared with a single unit. In the embodiment of FIG. 3 four units 24 are used. By using more than one unit means at least two units simultaneously and by anchoring that units independently at the frame the overall-stress exerted on the curtain is dispatched and the stress exerted on each unit is reduced.

By using the 360°-loop at each end of the units the tightness or degree of slack can be adjusted by passing the unit through different slits of the same arm.

Figure 4:
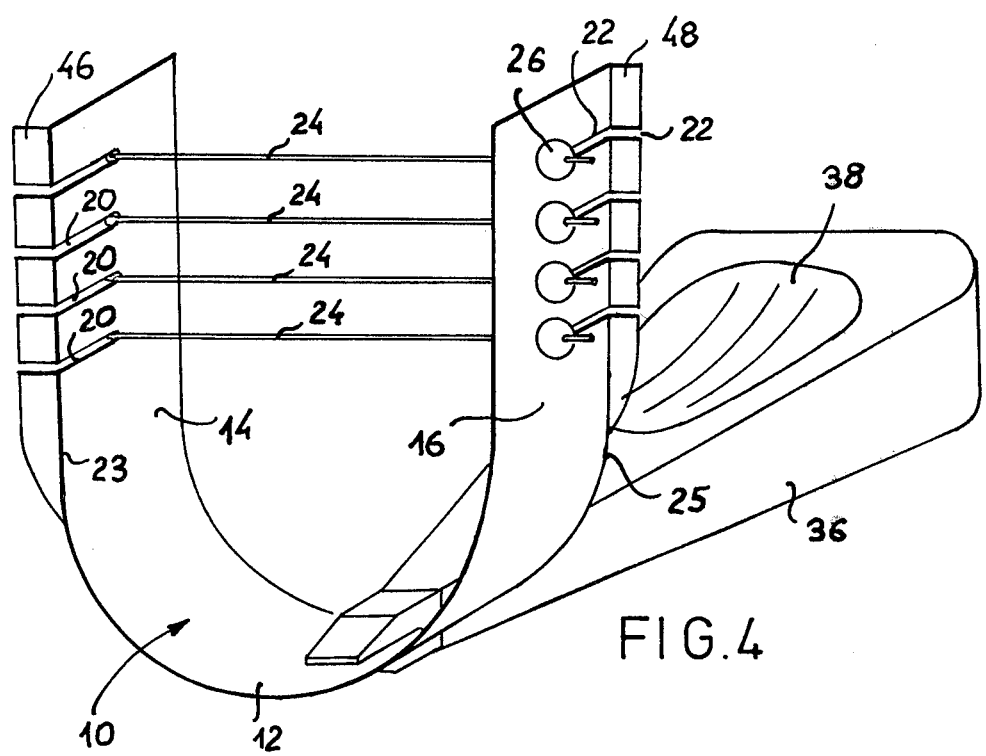
FIG. 4 is a perspective view of a further embodiment of an applicator.

FIG. 4 shows an alternative embodiment of an applicator 10 at which a plurality of parallel dental floss units can be fastened but which allows a different fastening mode. The slits 20 of the arm 14 extend from the front longitudinal edge 23 but the slits 22 of the arm 16 extend from the diagonally offset rear edge 25. Thereby units 24 of predetermined equal length can be fastened in a simple manner by hanging the ends of all units into the slits 20 of arm 14 respectively and after having compressed the arms are slipped into the slits 22 of arm 16. Then the arms are released and the units are tightened. The actual length of the units 24 must be substantially equal with the interspace of the arms. Even when the units 24 are lengthened in use they hardly can get out of the slits during operation. Flanges 46, 48 extending outwardly from the edges 23 and 25 respectively are provided as a further security to hold the units in their slits, and it should be clear that the slits in this case are L-shaped and extend from the longitudinal outer edge of the flanges over the width of the flanges into the arms respectively.

I claim:

1. A dental floss applicator comprising a substantially U-shaped frame of resilient material having a pair of substantially parallel arms, each one of said arms provided with a slit for holding a unit length of dental floss provided with caps or beads at both ends of which, characterized in that a plurality of slits are provided in each one of the arms, the slits of each arm extend parallely with one another and angularly with respect to the longitudinal direction of the arm, the slits of each arm have their inlet openings at one of the longitudinal edges of each arm and extend substantially cross-wise and end at a middle region of the arm and the plurality of slits of both arms are spaced equally in order to hold a plurality of unit lengths of dental floss in parallel relationship forming a dental floss curtain.

2. A dental floss applicator as claimed in claim 1, wherein the plurality of slits of one arm open from that longitudinal edge of which which lies diagonally opposite to that longitudinal edge from which the slits of the other arm extend.

3. A method for anchoring a unit length of dental floss having caps or beads at its ends in cross-wise extending slits of a pair of arms of a substantially U-shaped frame of resilient material, the method comprising the following steps: inserting the unit length of dental floss into the slit of one arm until the cap or bead of which contacts the arm; having a unit length of dental floss initially in the slit, thereafter completely turning around that part of the arm the width of which being reduced with respect to the overall width of the arm by the cross-wise extension of the slit forming at least a 360° loop and then passing through the same slit or an adjacent second slit of the same arm; said method being further defined by compressing the arms to reduce the distance therebetween; turning the other end of the dental floss at least by 180° and releasing the frame in order to bring the cap or bead at this end of the dental floss in contact with the other arm.

4. A unit length of dental floss for use in a method as claimed in claim 3, wherein the interspace between the caps or beads at the ends of the unit length of dental floss has an over-dimension with respect to the space between the opposite surfaces of the arms of the frame.

5. A unit length of dental floss as claimed in claim 4, wherein in the tensioned operating condition of the frame the over-dimension is at least equal with the double width of that portion of one arm which—as compared with the overall width of the arm—is reduced by the slit length.

* * * * *